(12) United States Patent
Boswell et al.

(10) Patent No.: US 6,399,828 B1
(45) Date of Patent: Jun. 4, 2002

(54) PREPARATION OF AMPHETAMINES FROM PHENYLPROPANOLAMINES

(75) Inventors: Robert Frederick Boswell, Richmond; Young Sek Lo, Chester, both of VA (US)

(73) Assignee: Boehringer Ingelheim Chemicals, Inc., Petersburg, VA (US)

( * ) Notice: Subject to any disclaimer, the term of this patent is extended or adjusted under 35 U.S.C. 154(b) by 0 days.

(21) Appl. No.: 10/020,488

(22) Filed: Oct. 29, 2001

(51) Int. Cl.$^7$ .............................................. C07C 209/00
(52) U.S. Cl. ...................... 564/375; 564/381; 564/374; 560/239; 560/232; 560/106; 560/105; 560/254
(58) Field of Search ................................ 564/374, 375, 564/381; 560/239, 232, 106, 105, 254

(56) References Cited

U.S. PATENT DOCUMENTS 6,232,475 B1 * 5/2001 Muller et al. ................ 564/374

\* cited by examiner

*Primary Examiner*—Samuel Barts
(74) *Attorney, Agent, or Firm*—Robert P. Raymond; Timothy X. Witkowski

(57) ABSTRACT

A process for making compound of formula I

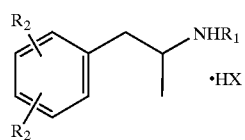

from a phenylpropanolamine salt of formula II

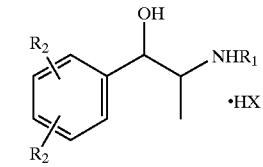

wherein:

$R_1$ is hydrogen or a lower alkyl group;

each $R_2$ is independently a hydrogen, halogen, lower alkyl group, lower alkoxy groups, lower alkyl group substituted with 1 to 5 halogens, lower alkoxy groups substituted with 1 to 5 halogens, or both $R_2$ together when on adjacent carbons constitute a —O(CH$_2$)$_x$O— where x is 1 to 4, thereby forming a ring structure fused with the phenyl group;

$R_3$ is a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl; and HX is an equivalent of an organic or inorganic acid, the process comprising:

(a) acylating the phenylpropanolamine salt of formula II with an acylating agent in a solvent at elevated temperature to make a reaction mixture containing an O-acylated phenylpropanolamine salt of formula III which can be isolated by the addition of a crystallization solvent, or optionally this mixture can be used in the next step; and (b) hydrogenating the O-acylated phenylpropanolamine salt to make the compound of formula I in the presence of a catalyst.

54 Claims, No Drawings

PREPARATION OF AMPHETAMINES FROM PHENYLPROPANOLAMINES

BACKGROUND OF THE INVENTION

The instant invention relates to a novel process for the synthesis of amphetamine, methamphetamine, and related compounds from derivatives of phenylpropanolamine acid addition salts. This new process, applied to produce d-amphetamine, has several advantages over prior art d-amphetamine production routes: shorter cycle times, less labor-intensive steps, and better chemical hygiene. Certain combinations of pharmaceutically acceptable salts of d,l-amphetamine and d-amphetamine are useful in the treatment of attention deficit disorders.

Many methods of making amphetamine and related compounds are known in the prior art, including the commercially used Leukart-Wallach reaction for producing racemic amphetamine from phenylacetone. For example, in one commercial process, phenylacetone is reacted with formamide and formic acid to form (±)-N-formylamphetamine (racemic N-formylamphetamine). The racemic N-formylamphetamine is then hydrolyzed with sulfuric acid, the solution basified, and the resulting d,l-amphetamine ((±)-amphetamine; racemic amphetamine) is distilled with an overall yield of about 60%.

In the illegal syntheses of amphetamine and related compounds, such as those found on internet searches, phenylpropanolamine and pseudoephedrine, isolated from over-the-counter cough and cold products, are converted to amphetamine and methamphetamine respectively (see, for example, Otto Snow, *Amphetamine Synthesis* (Thoth Press: Spring Hill, Fla., 1998); http://www.hyperreal.org/drugs/synthesis/meth.synth.; or http://hive.lycaeum.org/bookstore.htm/). Following one of the procedures used in illegal manufacture of amphetamine and related compounds, d,l-norephedrine was refluxed with hydriodic acid and red phosphorus to obtain a mixture of amphetamine and a compound believed to be a bis compound, 1-phenyl-2-(phenylisopropyl)aminopropane, in equal parts. By another procedure, heating norephedrine with thionyl chloride at reflux temperature, followed by catalytic hydrogenation of the resulting 2-amino-1-chloro-1-phenylpropane hydrochloride, gave amphetamine. To avoid the hazards of working with thionyl chloride, hydriodic acid, and red phosphorus, another route was desirable. The conversion of the hydroxyl group of phenylpropanolamine to a benzylic acyloxyester followed by removal by hydrogenolysis, the process of the instant invention, was investigated and found to be a good route. These three discrete synthetic routes are summarized in the examples of Scheme 1, with a process of the invention illustrated as the bottom pathway. In this Scheme, amphetamine is used for illustration only, these synthetic routes are applicable to related compounds with substitution patterns obvious to those skilled in the art.

Scheme 1

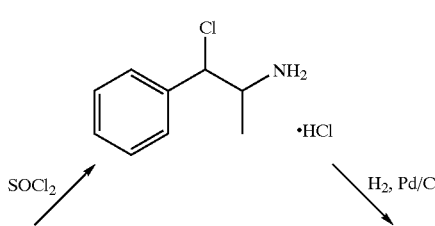

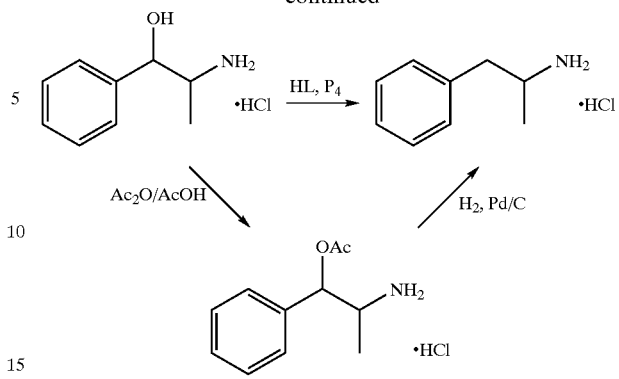

Currently, dextroamphetamine is obtained from racemic amphetamine through a lengthy, labor-intensive process. It is obtained in 23% yield from racemic amphetamine via tartrate salt resolution followed by basification and distillation. In the tartrate salt resolution step, a hot solution of 37% hydrochloric acid, methanol, tartaric acid, and the racemic amphetamine is drained from a reactor into stainless steel pots, and the hot mixture is allowed to cool undisturbed for 16 hours while the d-amphetamine tartrate salt predominantly crystallizes. The solvent is then decanted from each of the stainless steel pots and the recovered d-amphetamine tartrate salt is transferred by hand to a centrifuge, where the salt is spun dry, reslurried with methanol, and centrifuged dry again. The tartrate resolution step is then repeated until the salt obtained meets the melting point and optical rotation specifications desired.

Using the process of the invention, dextroamphetamine (S-(+)-amphetamine) can be stereospecifically prepared from a phenylpropanolamine having the S configuration at the carbon bearing the amino group, e.g., 1R,2S-(−)-norephedrine or 1S,2S-(+)-norpseudoephedrine (the erythro form of phenylpropanolamine is norephedrine and the threo form is norpseudoephedrine). In the process of the invention, the otherwise higher cost of the appropriate phenylpropanolamine diastereomers useful for preparing dextroamphetamine is offset by the shorter cycle times, a less labor-intensive process, and better chemical hygiene.

SUMMARY OF THE INVENTION

The process comprises ester formation and then removal of the benzylic acyloxy group by catalytic hydrogenation or catalytic transfer hydrogenation. As pointed out above, when it is applied to the production of d-amphetamine, the process has several advantages over current d-amphetamine production routes: shorter cycle times, less labor-intensive steps, and better chemical hygiene. Further optimization of yields and operation cycle times using optimization methods known to those skilled in the art would only increase these advantages.

The general process is shown in Scheme 2 below.

Scheme 2

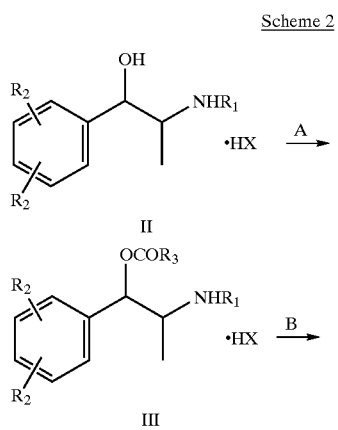

In Scheme 2, $R_1$ is hydrogen or a lower alkyl group;

each $R_2$ is independently a hydrogen, halogen, lower alkyl group, lower alkoxy group, lower alkyl group substituted with 1 to 5 halogens, lower alkoxy group substituted with 1–5 halogens, or both $R_2$ together when on adjacent carbons constitute a —$O(CH_2)_xO$— group where x is 1 to 4, thereby forming a ring structure fused with the phenyl group;

$R_3$ is a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl; and HX is an equivalent of an organic or inorganic acid, preferred acids include hydrofluoric acid, hydrochloric acid, hydrobromic acid, hydroiodic acid, sulfuric acid, phosphoric acid, nitric acid, formic acid, acetic acid, propionic acid and other carboxylic acids such as benzoic acid, tartaric acid, succinic acid, aspartic acid, saccharic acid, oxalic acid, malic acid, and the like.

In step A, the phenylpropanolamine salt starting material of formula II is acylated with an acylating agent, in this example, $(R_3CO)_2O$ in $R_3CO_2H$, to form the corresponding acylated phenylpropanolamine salt of formula III in a solvent at elevated temperature. In step B, the acylated phenylpropanolamine salt of formula III is hydrogenated using catalytic hydrogenation or catalytic transfer hydrogenation to obtain a compound of formula I.

For a direct route to dextroamphetamine, both b 1R,2S-(−)-norephedrine and 1S,2S-(+)-norpseudoephedrine have the correct steric configuration at the carbon bearing the amino group necessary to produce d-amphetamine [S-(+)-amphetamine] as shown in Scheme 3. 1R,2S-(−)-norephedrine is generally commercially available. This same process produces d-methamphetamine starting with either 1R,2S-(−)-ephedrine or 1S,2S-(+)-pseudoephedrine.

Scheme 3

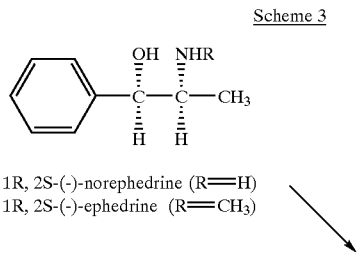

1R, 2S-(−)-norephedrine (R═H)
1R, 2S-(−)-ephedrine (R═CH₃)

-continued

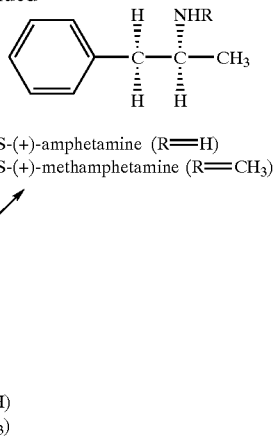

2S-(+)-amphetamine (R═H)
2S-(+)-methamphetamine (R═CH₃)

1S, 2S-(+)-norpseudoephedrine (R═H)
1S, 2S-(+)-pseudoephedrine (R═CH₃)

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

In the groups, radicals, or moieties defined below, the number of carbon atoms is often specified preceding the group, for example, $C_1$–$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk—Ar—, while "arylalkyl" means a monovalent radical of the formula Ar—Alk— (where Alk is an alkyl group and Ar is an aryl group). Furthermore, the use of a term designating a monovalent radical where a divalent radical is suitable shall be construed to designate the divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical having 1–10 carbons. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical of 2–10 carbons containing at least one carbon-carbon double bond. This term is exemplified by groups such as ethenyl, propenyl, n-butenyl, isobutenyl, 3-methylbut-2-enyl, n-pentenyl, heptenyl, octenyl, cyclohexylbutenyl, decenyl, and the like.

The terms "alkynyl" or "alkynyl group" mean a branched and straight-chain aliphatic hydrocarbon monovalent radical of 2–10 carbons containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkoxy" or "alkoxy group" mean a monovalent radical of the formula AlkO— where Alk is an alkyl group. This term is exemplified by groups such as methoxy, ethoxy, propoxy, isopropoxy, butoxy, sec-butoxy, tert-butoxy, pentoxy, and the like.

The terms "aryloxy" or "aryloxy group" mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula —C(O)Alk, where Alk is alkyl or hydrogen.

The terms "aryl" or "aryl group" mean a substituted or unsubstituted aromatic carbocyclic monovalent or divalent radical of from 6 to 14 carbon atoms having a single ring (e.g., phenyl or phenylene) or multiple condensed rings (e.g., naphthyl or anthryl). Unless otherwise specified, the aryl ring may be attached at any suitable carbon atom which results in a stable structure and, if substituted, may be substituted at any suitable carbon atom with one or more substituents selected from halogen, alkyl, alkoxy, aryl, acyl, nitro, cyano, and the like which results in a stable structure. Exemplary aryl groups include phenyl, naphthyl, anthryl, phenanthryl, indenyl, heptalenyl, biphenyl, biphenylenyl, azulenyl, pentalenyl, and the like. It may be abbreviated "Ar".

The terms "arylcarbonyl", "arylcarbonyl group", "aroyl" or "aroyl group" mean a monovalent radical of the formula —C(O)Ar, where Ar is aryl as defined above.

The terms "acyl" or "acyl group" mean a monovalent radical of the formula —C(O)R, where R is a substituent selected from hydrogen, alkyl, alkenyl, alkynyl, aryl, arylalkyl, cycloalkyl, and the like, each may be optionally substituted with one or more groups selected from halogens, alkoxy, hydroxy, nitro, cyano, alkyl aryl, and the like. Preferably R is a lower alkyl or phenyl, each optionally substituted. As such, the terms comprise alkylcarbonyl groups and arylcarbonyl groups.

The term "acylating agent" means a reactant that, when reacted with a compound having a nucleophilic site capable of reaction with the acylating agent, causes an acyl group to be covalently bound to one or more sites on the compound. Acylating agents include, but are not limited to, reagents having the formula RC(O)X, in which X is a halogen, an acyloxy group of formula R'C(O)O—, where R' has the same meaning of the R group defined in the previous paragraph. As such, the term encompasses carboxylic acids, carboxylic acid anhydrides, lower esters of carboxylic acids, and acid halides. Preferably, the acylating agents are acid halides or acid anhydrides. Such acylating agents may be mono-, di-, tricarboxylic, or polycarboxylic acylating agents. The acid anhydrides may be symmetrical, asymmetrical, or mixed anhydrides. In addition, acylating agents include in situ-generated o-acyl isoureas, compounds produced from the reaction of an acid (e.g., bromoacetic acid) and a carbodiimide (e.g., DIC and DCC), and isolated o-acyl isoureas. Exemplary and preferred acylating agents include acetyl chloride, acetyl bromide, propionyl chloride, benzoyl chloride, acetic anhydride, propionic anhydride, butyric anhydride, valeric anhydride, hexanoic anhydride, formic acetic anhydride, benzoic anhydride, trifluoroacetylchloride, methyl trifluoroacetate, ethyl trifluoroacetate, and the like.

The term "acetylating agent" means an acylating agent wherein the acyl group is acetyl.

The terms "acylation", "acylating", and the like refer to a chemical reaction whereby an acyl group is added to another compound or moiety using an acylating agent.

The terms "acetylation", "acetylating", and the like refer to a chemical reaction whereby an acetyl group is added to another compound or moiety using an acetylating agent.

The term "aliphatic group" means a non-aromatic straight or branched chain hydrocarbon group. As such, the term comprises alkyl, alkenyl, and alkynyl groups.

The term "alicyclic group" means a non-aromatic cyclic hydrocarbon group. As such, the term comprises cycloalkyl, cycloalkenyl, and cycloalkynyl groups.

The term "carboxylic acid" means an organic acid of the formula RC(O)OH, where R is a substituent selected from hydrogen or a substituent selected from a lower aliphatic group, lower alicyclic group, an aryl group, an aryl-alkyl group, or an alkyl-aryl group optionally substituted by halogen, alkyl, alkoxy, aryl, etc. This term is exemplified by formic acid, acetic acid, propanoic acid, butanoic acid, 2-methylpropanoic acid, pentanoic acid, propenoic acid, 2-methylpropenoic acid, 2-butenoic acid, cinnamic acid, benzoic acid, cyclobutanecarboxylic acid, salicylic acid, and the like.

The term "dicarboxylic acid" means an organic acid of the formula $R(C(O)OH)_2$, where R is either a bond (i.e., oxalic acid) or a divalent hydrocarbon group selected from a $C_1$–$C_6$ alkylene group optionally substituted with hydroxy, halogen, alkoxy, and the like, lower alicyclic group, an aryl group, an aryl-alkyl group, or an alkyl-aryl group. This term is exemplified by oxalic acid, malonic acid, succinic acid, glutaric acid, adipic acid, maleic acid, fumeric acid, phthalic acid, isophthalic acid, terephthalic acid, saccharic acid and the like.

The term "tricarboxylic acid" means an organic acid of the formula $R(C(O)OH)_3$, where R is either a bond (i.e., oxalic acid) or a substituent selected from a lower aliphatic group, lower alicyclic group, an aryl group, an aryl-alkyl group, or an alkyl-aryl group optionally substituted with hydroxy, halogen, alkoxy, and the like. This term is exemplified by citric acid.

The terms "alkylcarbonyloxy" or "alkylcarbonyloxy group" mean a monovalent radical of the formula —OC(O)Alk, where Alk is alkyl optionally substituted with hydroxy, halogen, alkoxy, and the like.

The terms "arylcarbonyloxy" or "arylcarbonyloxy group" mean a monovalent radical of the formula —OC(O)Ar, where Ar is aryl optionally substituted with hydroxy, halogen, alkoxy, and the like.

The term "precious metal catalyst" means a solid metal catalyst in whatever form suitable and effective for achieving the hydrogenation reactions of the instant invention. Exemplary and preferred precious metal catalysts include platinum, palladium, ruthenium, osmium, iridium, rhodium, and the like, or mixtures thereof, the metal or alloy provided in the form of: (a) a finely divided (e.g., powder, granules, etc.) or high surface area (e.g., porous, sponge, gauze platinum or palladium black) metal or alloy, (b) a precursor compound (e.g., the oxide) converted into the active catalyst before or during hydrogenation, or (c) distributed on an inorganic support, generally of high surface area, such as carbon, activated carbon, silica, alumina, or other metal oxides (e.g., calcium oxide), metal carbonates (e.g., calcium carbonate), metal sulfates (e.g., barium sulfate), or the like, wherein the supported precious metal is preferably present at 0.5 wt. % to 10 wt. %, more preferably 1 wt. % to 5 wt. %.

EXPERIMENTAL RESULTS

In the following experiments the analytical methods used include quantitative and qualitative analyses performed by high performance liquid chromatography (HPLC) and gas-liquid chromatography (GLC) methods.

I. Prior Art Synthesis Methods

For comparison purposes, the two prior art synthesis methods mentioned hereinabove were tested and the results obtained.

1. Iodination of Norephedrine Hydrochloride and Reduction to Amphetamine

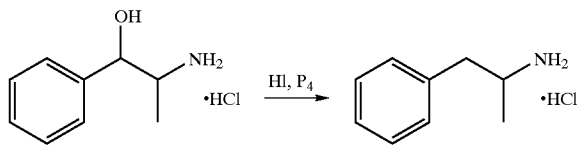

A 100 mL round bottom flask with a magnetic stirrer was charged with 20 mL 57% HI solution. (1R,2S)-(–)-norephedrine (10.0 g, 0.066 mol) was then added to the flask with stirring. Red phosphorus (1.0 g) was added to the stirred mixture and the reaction mixture temperature then increased to 40° C. within a few minutes. The reaction mixture was then heated to 100° C. and samples were withdrawn at intervals for HPLC analysis. The results were as follows:

a. 2 hours (58% norephedrine, 6.8% amphetamine, 6% bis compound);
   b. 4 hours (50% norephedrine, 10.2% amphetamine, 14.7% bis compound);
   c. 6 hours (41% norephedrine, 15.6% amphetamine, 17.7% bis compound); and
   d. 22 hours (48.95% amphetamine, 48.5% bis compound).

After 22 hours at 100° C., the reaction mixture was cooled and filtered to remove the phosphorus. An oily layer separated (1.3 g, identified by GLC as bis compound). The aqueous layer was basified with 50% sodium hydroxide solution and extracted with ether. The ether extract was dried over anhydrous magnesium sulfate and concentrated to obtain 4.1 g of yellow oil, identified by HPLC as consisting of 83.23% amphetamine and 16.27% bis compound). The calculated yield of amphetamine was therefore 3.41 g (38.3%)

2. Preparation of 2-Amino-1-chloro-1-phenylpropane Hydrochloride from Norephedrine Hydrochloride and Reduction to Amphetamine

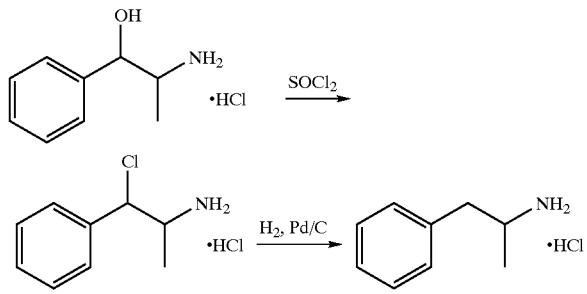

A 100 mL round bottom flask with a magnetic stirrer was charged with thionyl chloride (24.47 g, 15 mL) and norephedrine hydrochloride (5.38 g). The mixture was stirred and heated at reflux temperature for about 1 hour and allowed to cool to ambient temperature. The excess thionyl chloride was removed by evaporation on a rotary evaporator. The residue in the flask was triturated with ether (50 mL) and the solid collected. The crude solid product was recrystallized from methanol-isopropyl ether and the purified solid collected (2.83 g, 48%). The purified 2-amino-1-chloro-1-phenylpropane hydrochloride was then subjected to hydrogenolysis as follows. A solution of 2-amino-1-chloro-1-phenylpropane hydrochloride (2.38 g, 0.0137 mol) in a mixture of 50 mL ethanol/16 mL water was prepared and transferred to a Parr bottle. Under a nitrogen atmosphere, a portion of 10% palladium on carbon catalyst was added to the solution in the Parr bottle. The Parr bottle was then installed on a Parr shaker apparatus and an inert atmosphere produced and maintained in the bottle. The Parr bottle was then pressurized with hydrogen to about 50 psi and was shaken until the hydrogen uptake ceased. The contents of the Parr bottle was filtered to remove the catalyst and the filtrate was evaporated under reduced pressure to remove the ethanol. The remaining aqueous solution was basified with 50% sodium hydroxide solution. The oily top layer with was extracted with ether and the ether layer was separated from the aqueous layer. The ether extract was dried with drying agent and filtered to remove the drying agent. The filtrate was concentrated to obtain crude amphetamine as an oil (1.70 g, 72.3%).

II. The Process of the Invention

The process of the invention and experimental results using the process of the invention are discussed below. Norephedrine hydrochloride is commercially available and was used to illustrate in the reactions useful in this process. These conditions can also be applied to ephedrine hydrochloride or pseudoephedrine hydrochloride to produce d-methamphetamine. Furthermore, those skilled in the art should know to apply this process for the preparations of many amphetamine related compounds as covered in Scheme 2. Literature procedures for making amphetamine and methamphetamine report retention of configuration at the carbon bearing the amino group (see, e.g., Noggle, DeRuiter, and Clark, *J. Chrom. Sci.* 25, 38–42 (1987); Allen and Kiser, *J. Forensic Sciences* 32(4), 953–962 (1987)). Therefore d,l-norephedrine and d,l-norpseudoephedrine are expected to give the same product, d,l-amphetamine, and 1R,2S-(–)-norephedrine and 1S,2S-(+)-norpseudoephedrine are expected to give dextroamphetamine [d-amphetamine, S-(+)-amphetamine]. Also, d,l-ephedrine and d,l-pseudoephedrine are expected to give the same product, d,l-methamphetamine, and 1R,2S-(–)-ephedrine and 1S,2S-(+)-pseudoephedrine are expected to give dextromethamphetamine [d-methamphetamine, S-(+)-methamphetamine]. Abbreviations used in the following tables are NE for norephedrine, O-AcNE for O-acetylnorephedrine, N-AcNE for N-acetylnorephedrine, O,N-diAcNE for O,N-diacetylnorephedrine, Amp for amphetamine, and N-AcAmp for N-acetylamphetamine. These compounds were synthesized and used as references for HPLC analyses.

A. Preparation of 2-Amino-1-acetoxy1-phenylpropane Hydrochloride (O-Acetylnorephedrine) from Norephedrine Hydrochloride

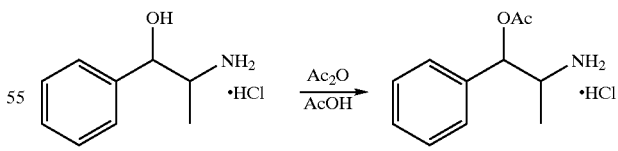

A three-necked 100 mL round bottom flask equipped with thermocontroller, stirrer, condenser, and gas bubbler was charged with 18.77 g (0.10 mol) d,l-norephedrine hydrochloride, acetic acid (18 mL), and acetic anhydride (12.24 g, 0.12 mol). The reaction mixture was warmed with a heating mantle with thermocontroller set for 80° C. After the reaction mixture cleared, it was held at 80° C. for 2 hours. Heptane (36 mL) was added to the 80° C. reaction mixture slowly with rapid stirring, then the mixture was allowed to cool to ambient temperature. The slurry was stirred overnight at ambient temperature and the solid was collected by filtration. The granular solid was dried under ambient conditions overnight to obtain 18.13 g of product (89.99% yield).

B. Preparation of 2-Amino-1-acetoxy-1-phenylpropane Hydrochloride (O-Acetylnorephedrine) from Norephedrine Hydrochloride and Reduction to Amphetamine without Isolation of the Intermediate

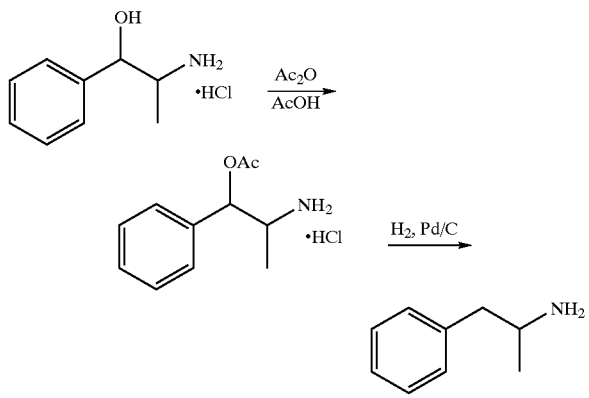

The following method is an example wherein the reduction of the intermediate O-acetylnorephedrine is performed without isolating the O-acetylnorephedrine.

A 100 mL 3-necked round bottom flask equipped with a magnetic stirrer, condenser, and thermocontroller, was charged with d,l-norephedrine hydrochloride (9.39 g, 0.050 mol), acetic anhydride (6.12 g, 0.060 mol), and acetic acid (18 mL). The reaction mixture is heated with heating mantle with a thermocontroller set at 80° C. When the temperature reached about 60° C., the reaction mixture became exothermic and the temperature rose to 84° C. The reaction mixture was cooled to 80° C. and held at 80° C. for 2 hours. HPLC analysis of reaction mixture at this point showed 90.69% O-acetylnorephedrine and 6.88% O,N-diacetylnorephedrine. The reaction mixture was stirred overnight at ambient temperature and then diluted with 20 mL ethanol. The resulting solution was transferred to a Parr bottle, which was purged with nitrogen gas and about 1 g of 10% palladium-carbon catalyst (50% water) was added. The Parr bottle was installed on a Parr shaker apparatus and inerted with nitrogen. The Parr bottle was then pressurized with hydrogen to 45 psi and then shaken under hydrogen pressure at ambient temperature. In 10 minutes a 3 psi pressure drop was observed. The Parr bottle temperature controller was set to 55° C. and the pressure increased from 42 psi to 47 psi. The pressure changes over the next 5 to 6 hours were recorded. The heat was then turned off and the reaction mixture was allowed to cool to ambient temperature. The final pressure was recorded and the Parr bottle was depressurized and purged with nitrogen gas. The mixture was filtered to remove the catalyst and the filtrate was analyzed and found to consist of 2.45% norephedrine, 57.59% amphetamine, 20.71% O-acetylnorephedrine, 10% N-acetylamphetamine, and 3.75% O,N-diacetylnorephedrine. The calculated yield was 3.89 g (57%)

C. Further Examples of Acetylation of Norephedrine Hydrochloride

As illustrated above, O-acetylnorephedrine hydrochloride can be prepared in good yield from norephedrine hydrochloride by heating with acetic anhydride (preferably 1.2 to 2.0 equivalents) in acetic acid (preferably 1 to 2 mL/g of norephedrine hydrochloride) in a mildly exothermic reaction at 50–80° C. for 2 hours, although exothermic reaction temperatures could exceed 80° C. Generally, when less than a 20% excess of acetic anhydride is used, some unreacted norephedrine remains, for example, when a 10% excess of acetic anhydride was used, it reacted with only about 80% of the norephedrine hydrochloride. It was found that the amount of acetic acid used does not appear to be critical, as the reaction proceeded well with either 1 or 2 mL/g of norephedrine hydrochloride and could be agitated without difficulty at 1 mL/g. When no acetic acid was used, however, the product obtained consisted of a mixture 16.71% norephedrine, 67.08% O-acetylnorephedrine, and 14.43% O,N-diacetylnorephedrine. Results of other laboratory preparations are summarized in Table 1.

TABLE 1

Summary on Acetylations of Norephedrine Hydrochloride

| Experiment | % Yield | % O-AcNE | % Amp | % N-AcNE | % NE | % N-AcAmp | % O,N-diAcNE |
|---|---|---|---|---|---|---|---|
| A | * | 90.8 | — | — | <1 | — | 6.3 |
| C | 80.1 | 92.98 | — | — | — | — | 3.74 |
| D | 52.2 | 98.43 | — | — | 1.57 | — | — |
| E | 26.8 | 97.5 | — | — | 2.5 | — | — |
| F | 85.5 | 95.7 | — | — | — | — | — |
| G | 56.9 | 100 | — | — | — | — | — |
| H | 95.2 | — | — | — | — | — | — |
| I | 90.0 | — | — | — | — | — | — |
| L | 82.7 | 89.44 | 0.832 | — | — | — | 9.06 |
| Z | 99.18 | 89.39 | — | — | — | — | — |

* Product was not isolated: reaction mixture carried on to reduction step (Experiment B, Tables 3, 4, and 7).

(i). Side Products

Table 1 lists the side products found in various acetylation experiments. Small amounts of unreacted norephedrine and O,N-diacetylnorephedrine, were found as side products in the isolated products. The signal for amphetamine in experiment L may be an artifact.

(ii). Crystallization Solvent

To increase the rate of crystallization of the O-acetylnorephedrine hydrochloride salt and aid in removing acetic acid and any excess acetic anhydride that may be present, the reaction mixture was treated with heptane (Experiment I), methyl tert-butyl ether (Experiments F and H), ethanol (Experiment G), isopropanol, methyl isobutyl ketone, acetonitrile, ethyl acetate, tetrahydrofuran, or other solvent in which the product has little solubility. The solid product that formed was collected by filtration. Heptane is a preferred solvent, as the solid produced was dense and did not appear to be solvated as much as with other solvents tried.

(iii). Rate of the Acetylation Reaction

The rate of the acetylation reaction is demonstrated by the results of high performance liquid chromatography analyses (HPLC) of a reaction at various time intervals (Experiment A). These results are given in Table 2 and show that the reaction is almost complete within 20 minutes of the reaction mixture becoming clear.

TABLE 2

O-Acetylation of (±)-Norephedrine Hydrochloride

| Time (minutes) | % NE | % N-AcNE | % O-AcNE | % O,N-diAcNE |
| --- | --- | --- | --- | --- |
| 0* | 21.14 | — | 71.68 | 4.79 |
| 20 | 3.48 | — | 89.53 | 5.49 |
| 40 | <2 | — | 91.91 | 6.11 |
| 90 | <1 | — | 90.92 | 6.47 |
| 120 | <1 | — | 90.80 | 6.30 |

*zero time: point at which the heated reaction mixture was observed to become clear (iv). Chemical Reactivities of Norephedrine Free Base and Salts The commercially available precursor to dextroamphetamine is 1R,2S-(−)-norephedrine. Attempts were made to O-acetylate the norephedrine free base, but produced mostly N-acetylamphetamine according to an analysis of the carbonyl region of the infrared spectra. In one experiment, norephedrine free base in acetic acid was treated with 0.5 equivalents of sulfuric acid and then treated with 1.1 equivalents of acetic anhydride with heating to 63° C. to obtain a clear solution. Catalytic reduction followed by basification gave an oil that was composed of 13.96% amphetamine and 68% norephedrine, an indication that the acetylation procedure on a sulfate salt was only partially successful. In another experiment, a 10 mol portion of norephedrine hydrochloride was acetylated with a 20% excess of acetic anhydride in 2 mL acetic acid/g of salt and progress of the reaction followed fours (Table 2). The reaction mixture was diluted with 130 mL water and subjected to catalytic hydrogenation for 22 hours to obtain 10.4 g of oil. The long reaction time is attributed to the presence of acetic acid in the reduction mixture. Yield of amphetamine from norephedrine hydrochloride based on the weight of product and HPLC analysis is 66% (Experiments A and B). For these experiments, it can be seen that the best results were obtained with the salts of phenylpropylamine or norephedrine, particularly the hydrochloride salt.

D. Catalytic Transfer Hydrogenation of O-Acetylnorephedrine

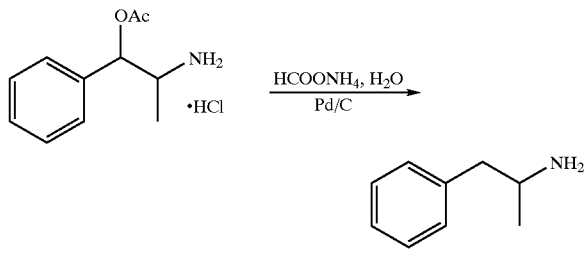

A 500 mL 3-necked round bottom flask equipped with stirrer, addition funnel, condenser, and thermocontroller was charged with O-acetylnorephedrine hydrochloride (47.0 g, 0.205 mol), 131 mL of water, and 1.0 g of 10% palladium on carbon (50% water) catalyst. A solution of ammonium formate (HCOONH$_4$; 15.50 g, 0.246 mol) in 20 mL water was then prepared. The reaction mixture in the 3-necked round bottom flask was then heated in a water bath temperature controlled to 71° C. When the reaction mixture temperature reached 68° C., approximately 6 mL of the ammonium formate solution was added in 2 mL increments to the reaction mixture at 5 minute intervals. When evolution of gas began to subside, the remainder of ammonium formate solution was added dropwise and the reaction mixture stirred in the water bath for approximately 1 hour. The water bath temperature controller was then turned off and the reaction mixture was allowed to cool to ambient temperature while stirring overnight. The cooled reaction mixture was then filtered to remove the catalyst and the filtrate was treated with 26 mL (0.50 mol) of 50% sodium hydroxide solution. The basified reaction mixture was then transferred to a separatory funnel and allowed to stand for 0.5 hour. The bottom aqueous layer was separated from the top oily layer and the oily layer was recovered (40.83 g). The oil was analyzed and the analysis had the following results: GLC weight-% assay: 60.18% amphetamine; Karl Fischer titration: 23.15% water; HPLC analysis: 79.03% amphetamine, 14.6% N-acetylnorephedrine, 5.49% N-acetylamphetamine, and 0.76% norephedrine; calculated yield: 24.6 g amphetamine (88.8%).

E. Catalytic Hydrogenation of O-Acetylnorephedrine Hydrochloride

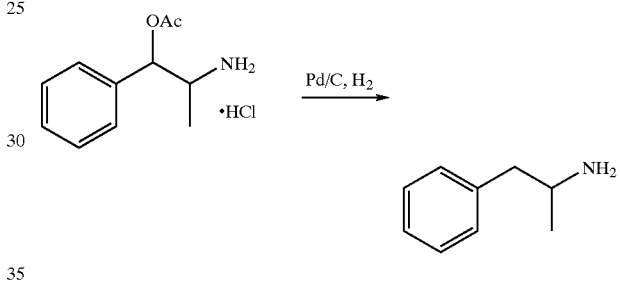

A Parr bottle was charged with O-acetylnorephedrine hydrochloride (11.43 g) and 75 mL of water. The Parr bottle was flushed with nitrogen and the catalyst added. The bottle was then shaken on a Parr apparatus with an initial pressure of 55 psi. After 2 hours, the pressure drop was 4 psi (on tank). The Parr bottle was shaken for another hour to ensure completion of hydrogenolysis and then depressurized and flushed with nitrogen. The contents of the Parr bottle was then filtered to remove the catalyst and the filtrate was basified with 15 mL of 50% sodium hydroxide solution and the mixture was allowed to stand overnight. The mixture was then transferred to a separatory funnel to separate the bottom aqueous layer from the top oily layer; the oily layer was recovered (7.00 g). The oil was analyzed and the analysis had the following results: GLC weight-% assay: 63.02% amphetamine; HPLC analysis: 87.22% amphetamine, 10.8% N-acetylnorephedrine, 0.37% N-acetylamphetamine; Karl Fischer analysis: 23.699% water; calculated yield: 4.41 g amphetamine (65.33%).

F. Further Examples of the Reduction of O-Acetylnorephedrine Hydrochloride to Amphetamine Reduction of O-acetylnorephedrine hydrochloride to amphetamine is accomplished by either catalytic hydrogenation or catalytic transfer hydrogenation. Catalytic hydrogenation can be achieved in about four hours at room temperature in water using 10% palladium on carbon catalyst (50% wet with water) at 50–55 psi hydrogen pressure on a Parr shaker. Using this method, most of the hydrogen uptake occurs within 2 hours. Catalytic transfer hydrogenation using ammonium formate and 10% palladium on carbon (50% wet with water) in water is complete in 20–30 minutes from initiation of the reaction if the ammonium formate solution is added in one portion.

1. Catalytic Hydrogenation

Results of laboratory hydrogenation Experiments are shown in Tables 3 and 4. In Table 4, the weight-% amphetamine was determined by GLC and the % composition was determined by HPLC.

TABLE 3

Reaction Conditions used in the Catalytic Hydrogenation of O-Acetylnorephedrine Hydrochloride

| Experiment | g (mol) | Solvent (mL) | mL/g | Time (hours) | Crude yield g (%) |
|---|---|---|---|---|---|
| AA | 10.04 (0.044) | H₂O (100) | 4.96 | 3.75 | 6.9 (>100%) |
| BB | 6.00 (0.026) | H₂O (50) EtOH (100) | 25 | 1.5 | 3.44 (98) |
| CC | 11.48 (0.05) | H₂O (100) | 8.7 | 4.5 | — |
| B | 22.95 (0.10)** | H₂O (114) HOAc (36) | 6.54 | 23 | 10.4 (77) |
| N | 11.48 (0.050) | H₂O (50) | 4.36 | 4 | 5.18(76.7) |
| T | 22.95 (0.10) | H₂O (70) | 3.05 | 22.5 | 13.65 (>100) |
| V | 11.45 (0.050) | H₂O (75) | 6.55 | 2 | 7.00 (>100) |
| Y | 22.95 (0.10) | H₂O (137) | 5.97 | 2 + 2* | 14.66 (>100) |

*Reduction judged to be >95% complete in 2 hours but given another 2 hours on Parr apparatus to make sure hydrogen uptake was complete.
**From Experiment A and thus may require a larger volume of solvent for hydrogenation to proceed readily (Experiment BB). If either acetic acid or ethanol is used, an extra step in the work-up to remove the organic solvent is necessary. This makes water an excellent solvent for the catalytic reduction as the volume is not excessive, it is not flammable, and it is inexpensive. Rigorous purging of the hydrogenation vessel with an inert gas before charging the palladium catalyst is not required with water, as it would be with a flammable solvent. The amphetamine obtained from Experiments T, V, and Y was separated from the aqueous solution after basification rather than extracting with a solvent. The crude amphetamine was shown by Karl Fischer water analysis to contain 23–24% water. This accounts for yields greater than 100% and lower weight-% amphetamine values.

2. Catalytic Transfer Hydrogenation

For catalytic transfer hydrogenation, a mixture of O-acetylnorephedrine hydrochloride, water, and 10% palladium on carbon (50% wet with water) can be treated with 1.2 equivalents of ammonium formate and heated until an exothermic reaction accompanied by evolution of gas occurs. The reaction is completed when the evolution of gas subsides. Results of Experiments using catalytic transfer hydrogenation are shown in Table 5. These reactions were done at temperatures between 60° C.–80° C. except for the higher temperature attained in the exotherm.

TABLE 4

Analysis of Catalytic Hydrogenation Products

| Experiment | % Yield (crude) | Wt % Amp | % O-AcNE | % Amp | % N-AcNE | % NE | % N-AcAmp | % O,N-diAcNE |
|---|---|---|---|---|---|---|---|---|
| B | 77* | 75.23 | — | 86.3 | 6.7 | 1.3 | 2.7 | 2.67 |
| N | 76.7 | 83.07 | — | 82.7 | 15.73 | 0.8 | 0.21 | — |
| T | 101 | 68.86 | — | 91.16 | 4.65 | 0.26 | 2.55 | — |
| V | 104 | 63.02 | — | 87.72 | 10.8 | 0.07 | 0.37 | — |
| Y | 109 | 73.12 | 0.32 | 93.92 | 4.79 | 0.63 | 0.24 | — |

*calculated from norephedrine hydrochloride

The solubility of O-acetylnorephedrine hydrochloride in water is 5.5 mL/g (Experiment X). Hydrogenation reactions at water concentrations equal to or more than 5.5 mL/g appear to be about 90–95% complete in 2 hours (Experiment T). The presence of acetic acid seems to retard the reduction (Experiment B). Ethanol reduces the solubility of the salt

TABLE 5

Catalytic Transfer Hydrogenation of O-Acetylnorephedrine Hydrochloride With Ammonium Formate

| Experiment | % Yield | Wt % Amp | % O-AcNE | % Amp | % N-AcNE | % NE | % N-AcAmp | % O,N-diAcNE |
|---|---|---|---|---|---|---|---|---|
| DD | 81.9 | 57.40 | — | — | — | — | — | — |
| M | 67.0 | 81.80 | — | 86.23 | 9.57 | — | 1.9 | — |
| O | 73.4 | 92.18 | — | 91.75 | 4.76 | 1.05 | 1.87 | — |
| P | 45.9 | — | — | 96.16 | 2.64 | 0.43 | 0.59 | — |
| Q | 83.6 | — | — | 90.19 | 7.91 | 0.63 | 0.84 | — |
| R | 89.3 | 71.52 | — | 88.86 | 7.87 | 0.92 | 1.97 | — |
| S | 90.4 | 70.0 | — | 81.19 | 13.84 | 0.43 | 4.22 | — |
| U | 147.0 | 60.18 | — | 79.03 | 14.60 | 0.76 | 5.49 | — |

The quantities of reactants for the catalytic transfer hydrogenation reactions presented in Table 5 are shown in Table 6.

TABLE 6

Reactant Quantities in Catalytic Transfer Hydrogenolysis

| Experiment | O-AcNE.HCl | Solvent* | Grams of Ammonium Formate (mol) | Crude Yield (% yield) | % Amp. | |
|---|---|---|---|---|---|---|
| DD | 4.98 g (0.0217 mol) | 100 mL methanol | 4.98 g (0.08 mol) | 2.4 g (81.9%) | 57.4 | Area-% |
| M | 4.98 g (0.0217 mol) | 10 mL water (AF) 10 mL MeOH (OACNE) | 5.03 g (0.08 mol) | 1.97 g (67%) | 86.2 | Area-% |
| O | 5.74 g (0.025 mol) | 20 mL water (OAcNE) 10 mL water (AF) | 3.15 g (0.05 mol) | 2.48 g (73.4%) | 92.18 | Wt-% |
| P | 5.74 g (0.025 mol) | 20 mL water (OAcNE) 10 mL water (AF) | 2.36 g (0.0375 mol) | 1.55 g (45.9%) | 96.16 | Area-% |
| Q | 5.74 g (0.025 mol) | 20 mL water (OAcNE) 10 mL water (AF) | 1.58 g (0.025 mol) | 2.82 g (83.6%) | 90.2 | Area-% |
| R | 11.48 g (0.05 mol) | 33 mL water (OAcNE) 20 mL water (AF) | 3.78 g (0.06 mol) | 6.03 g (89.3%) | 71.5 | Wt%** |
| S | 22.95 g (0.10 mol) | 69 mL water (OAcNE) 10 mL water (AF) | 7.56 g (0.12 mol) | 12.2 g (90.4%) | 70.0 | Wt%** |
| U | 47.0 g (0.205 mol) | 131 mL water (OAcNE) 20 mL water (AF) | 15.50 g (0.246 mol) | 40.87 g (147%) | 60.18 | Wt%** |

*2 volumes of solvent shown where ammonium formate (AF) solution is added to OAcNE.HCl solution separately
**amphetamine layer was separated without extraction into ether after basification When a large excess of ammonium formate is used, a white solid sublimes into the condenser. Sublimation was not observed with only a 10–20% excess of ammonium formate. A 10–20% excess of ammonium formate appears to be sufficient for complete reaction. The exotherm and evolution of gas were also seen at about 52° C. in Experiment DD that was conducted in methanol.

3. Comparison of Hydrogenolysis Reactions

In both types of the hydrogenolysis reactions, workup, with one exception, consists of filtering the reaction mixture to remove the palladium on carbon catalyst, basifying the filtrate to pH 14, separation of the aqueous layer from the amphetamine layer, and distillation of the amphetamine. That exception was Experiment DD where the filtered reaction mixture was concentrated and the residue taken up in water and basified. The two types of hydrogenolysis reactions are comparable in efficiency, with the catalytic transfer hydrogenation being the faster. However, there is a question of safety as there is an induction period with the catalytic transfer hydrogenation reaction accompanied by considerable evolution of gas when the reaction begins. The reaction can be partially controlled by initial addition of only about 25% of the ammonium formate as an aqueous solution and heating the mixture until the reaction begins. The remainder of the ammonium formate solution can then be added at a suitable rate.

Ammonium formate appears to catalyze the rearrangement of O-acetylnorephedrine hydrochloride to N-acetylnorephedrine. Three samples of O-acetylnorephedrine hydrochloride (Experiment Z recrystallized) were stirred with water for six hours respectively at room temperature, at 60° C., and at 60° C. with ammonium formate added. Samples were taken at intervals for HPLC analyses. At room temperature, the percentage of O-acetylnorephedrine hydrochloride decreased from 99.30 to 99.12% over a period of 6 hours and the percentage of N-acetylnorephedrine increased from 0.10% to 0.21%. At 60° C., the percentage of O-acetylnorephedrine hydrochloride decreased from 99.18 to 97.79 with the percentage of N-acetylnorephedrine increasing from 0.21% to 1.1% over a 6 hour period. With the ammonium formate mixture at 60° C., the percentage of O-acetylnorephedrine hydrochloride dropped to 91.23% within 30 minutes and to 77.20% by 6 hours while the amount of N-acetylnorephedrine increased from 7.51% to 20.95%. The catalytic hydrogenation route therefore appears to be preferable to catalytic transfer hydrogenation in view of the induction period, gas evolution, and rearrangement potential.

The amphetamine obtained from several of the hydrogenolysis reactions of both types was analyzed by HPLC and/or GLC and the results summarized in Table 7. The products of Experiments Experiment P and Experiment Q were obtained by extraction into ether and drying of the extract to remove any water. The product obtained in Experiments R, S, and U were shown by Karl Fischer analyses to contain water and is compensated for in the Weight-% amphetamine analyses. The percent yield of amphetamine is calculated from the actual weight of the product isolated and the percentage of amphetamine in the product as determined by GLC or HPLC weight-% analyses. The composition of the product is the area-% analysis.

TABLE 7

Crude and Actual Yields of Amphetamine from Both Reduction Methods

| Experiment | Reaction Size (mol) | Crude Yield (g) | Wt. % Amp. | Calc. Yield Amp. (g) | % Yield Amp. |
|---|---|---|---|---|---|
| B[1] | 0.10 | 10.4 | 75.23 | 7.82 | 58.0 |
| N[1] | 0.05 | 6.75 | 83.7 | 4.34 | 64.2 |
| T[1] | 0.10 | 13.65 | 68.86 | 9.35 | 69.6 |
| V[1] | 0.05 | 7.00 | 63.02 | 4.41 | 66.1 |
| Y[1] | 0.10 | 14.66 | 73.32 | 10.70 | 79.3 |
| M[2] | 0.022 | 1.97 | 81.8 | 1.61 | 55.0 |
| O[2] | 0.025 | 2.48 | 81.8 | 1.61 | 55.0 |
| P[2] | 0.025 | 1.55* | 96.16 | 1.44 | 42.8 |
| Q[2] | 0.10 | 2.82* | 90.2 | 2.54 | 75.4 |
| R[2] | 0.05 | 6.03 | 71.52 | 4.31 | 63.9 |
| S[2] | 0.10 | 12.2 | 70.0 | 8.54 | 63.3 |
| U[2] | 0.205 | 40.83 | 60.18 | 24.57 | 88.8 |

[1]catalytic hydrogenation
[2]catalytic transfer hydrogenation
*product obtained in these reactions by extraction into ether and drying extract Instead of having wt % amphetamine data, area % of amphetamine in product mixture was used to calculate expected yield of amphetamine. In other reactions, the product obtained was not dry.

All publications, patent applications, patents, and other references mentioned herein are incorporated by reference in their entirety. Furthermore, unless otherwise defined, all technical and scientific terms used herein have the same meaning as commonly understood by one of ordinary skill in the art to which this invention belongs.

As required, the above description includes the best mode presently contemplated for carrying out the invention. It will be noted that the invention has been described with reference to numerous specific embodiments and examples; it is emphasized that these embodiments and examples are not to be construed as limiting the invention but are made merely for the purpose of describing the general principles of the invention and illustrating the invention. Therefore, although suitable methods, apparatus, and materials for the practice or testing of the present invention are described above, other suitable methods, apparatus, and materials similar or equivalent to those described herein, which are well known in the art or will hereinafter be developed, can also be used without departing from the spirit or scope of the invention. As these various equivalents and substitutions will be recognized by those of ordinary skill in the art in view of the foregoing disclosure, they are contemplated to be within the scope of the present invention as defined by the appended claims. The appended claims solely define the scope of the invention.

We claim:

1. A process for making compound of formula I

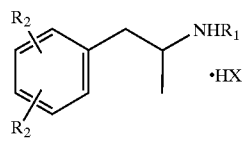

I from a phenylpropanolamine salt of formula II

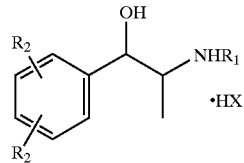

II through the intermediate compound of formula III

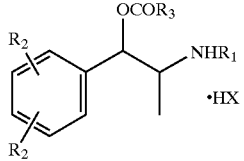

III wherein:

$R_1$ is hydrogen or a lower alkyl group;

each $R_2$ is independently a hydrogen, halogen, lower alkyl group, lower alkoxy groups, lower alkyl group substituted with 1 to 5 halogens, lower alkoxy groups substituted with 1 to 5 halogens, or both $R_2$ together when on adjacent carbons constitute a —O(CH$_2$)$_x$O— where x is 1 to 4, thereby forming a ring structure fused with the phenyl group;

$R_3$ is a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl; and HX is an equivalent of an organic or inorganic acid, the process comprising:

(a) acylating the phenylpropanolamine salt of formula II with an acylating agent in a solvent at elevated temperature to make a reaction mixture containing an O-acylated phenylpropanolamine salt of formula III which can be isolated by the addition of a crystallization solvent, or optionally this mixture can be used in the next step; and (b) hydrogenating the O-acylated phenylpropanolamine salt to make the compound of formula I in the presence of a catalyst.

2. The process of claim 1, wherein the acylating agent is selected from the group consisting of: acetic anhydride, acetyl chloride, propionic anhydride, propionyl chloride, butyric anhydride, and butyryl chloride.

3. The process of claim 1, wherein the acylating agent is a compound of formula $R_3C(O)X$, wherein:

X is a halogen; and $R_3$ is a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl.

4. The process of claim 3, wherein $R_3$ is a methyl group.

5. The process of claim 1, wherein the acylating agent is a compound of formula $R_3C(O)O(O)CR_3'$, wherein:

$R_3$ and $R_3'$ are independently a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl.

6. The process of claim 5, wherein $R_3$ and $R_3'$ are methyl groups.

7. The process of claim 1, wherein HX is selected from the group consisting of: hydrofluoric acid, hydrochloric acid, hydrobromic acid, hydroiodic acid, sulfuric acid, phosphoric acid, nitric acid, formic acid, acetic acid, propionic acid, benzoic acid, tartaric acid, succinic acid, oxalic acid, aspartic acid, saccharic acid, and malic acid.

8. The process of claim 1, wherein HX is a carboxylic acid, dicarboxylic acid, or tricarboxylic acid.

9. The process of claim 1, wherein the compound of formula I is amphetamine.

10. The process of claim 9, wherein the amphetamine is d,l-amphetamine.

11. The process of claim 9, wherein the amphetamine is S-(+)-amphetamine.

12. The process of claim 9, wherein the amphetamine is R-(−)-amphetamine.

13. The process of claim 1, wherein the compound of formula I is methamphetamine.

14. The process of claim 13, wherein the methamphetamine is S-(+)-methamphetamine.

15. The process of claim 13, wherein the methamphetamine is R-(−)-methamphetamine.

16. The process of claim 1, wherein acetic acid, propionic acid, or butyric acid is added to the phenylpropanolamine salt as solvent before or at the same time as the acylating agent.

17. The process of claim 1, wherein the hydrogenation step (b) is performed using catalytic hydrogenation.

18. The process of claim 17, wherein the catalytic hydrogenation is performed using a precious metal catalyst.

19. The process of claim 18, wherein the precious metal catalyst is selected from the group consisting of: platinum, palladium, ruthenium, osmium, iridium, rhodium, and mixtures thereof.

20. The process of claim 19, wherein the precious metal catalyst is in the form of a finely divided or high surface area metal or alloy.

21. The process of claim 19, wherein the precious metal catalyst is obtained by converting a precursor compound into the active catalyst before or during hydrogenation.

22. The process of claim 19, wherein the precious metal catalyst is distributed on an inorganic support.

23. The process of claim 20, wherein the inorganic support is selected from the group consisting of: carbon, activated carbon, metal oxides, metal carbonates, and metal sulfates.

24. The process of claim 18, wherein the precious metal catalyst is palladium on carbon.

25. The process of claim 1, wherein the hydrogenation step (b) is performed using catalytic transfer hydrogenation with a hydrogenation agent.

26. The process of claim 25, wherein the catalytic transfer hydrogenation is performed using a precious metal catalyst.

27. The process of claim 26, wherein the precious metal catalyst is selected from the group consisting of: platinum, palladium, ruthenium, osmium, iridium, rhodium, and mixtures thereof.

28. The process of claim 27, wherein the precious metal catalyst is in the form of a finely divided or high surface area metal or alloy.

29. The process of claim 28, wherein the precious metal catalyst is obtained by converting a precursor compound into the active catalyst before or during hydrogenation.

30. The process of claim 27, wherein the precious metal catalyst is palladium on carbon.

31. The process of claim 25, wherein the hydrogenation agent is selected from the group consisting of ammonium formate, formic acid, ammonium or metal salts of hypophosphite.

32. The process of claim 26, wherein the hydrogenation agent is selected from the group consisting of ammonium formate, formic acid, ammonium or metal salts of hypophosphite.

33. The process of claim 1, wherein the acetylated phenylpropanolamine salt obtained from step (a) is isolated before step (b) is performed.

34. The process of claim 33, wherein the acylated phenylpropanolamine salt obtained from step (a) is isolated by adding a crystallization solvent to the reaction mixture containing the acylated phenylpropanolamine salt.

35. The process of claim 34, wherein the crystallization solvent is selected from the group consisting of: pentane, hexane, heptane, octane, methyl tert-butyl ether, methyl isobutyl ketone, ethanol, propanol, isopropanol, butanol, and mixtures thereof.

36. The process of claim 35, wherein the crystallization solvent is heptane.

37. The process of claim 1, wherein the acylated phenylpropanolamine salt obtained from step (a) is not isolated before step (b) is performed.

38. The process of claim 1, wherein the carbon bearing the amino group in the phenylpropanolamine salt has the racemic configuration.

39. The process of claim 1, wherein the carbon bearing the amino group in the phenylpropanolamine salt has the S configuration.

40. The process of claim 1, wherein the phenylpropanolamine salt is selected from the group consisting of: 1R,2S-(−)-norephedrine, 1S,2S-(+)-norpseudoephedrine, 1R,2S-(−)-ephedrine, and 1S,2S-(+)-pseudoephedrine.

41. The process of claim 1, wherein the compound of formula I is S-(+)-methamphetamine and the phenylpropanolamine salt is selected from the group consisting of: 1R,2S-(−)-ephedrine and 1S,2S-(+)-pseudoephedrine.

42. The process of claim 1, wherein the amount of acylating agent used is between about 1.0 equivalents and 3.0 equivalents based on the amount of phenylpropanolamine salt.

43. The process of claim 42, wherein the amount of acylating agent used is between about 1.1 equivalents and 2.5 equivalents based on the amount of phenylpropanolamine salt.

44. The process of claim 43, wherein the amount of acylating agent used is between about 1.1 equivalents and 2.0 equivalents based on the amount of phenylpropanolamine salt.

45. The process of claim 44, wherein the amount of acylating agent used is between about 1.2 equivalents and 1.5 equivalents based on the amount of phenylpropanolamine salt.

46. The process of claim 1, wherein the temperature of the reaction mixture of step (a) is between 50° C. and 100° C.

47. The process of claim 46, wherein the temperature of the reaction mixture of step (a) is between 60° C. and 90° C.

48. The process of claim 47, wherein the temperature of the reaction mixture of step (a) is between 70° C. and 85° C.

49. The process of claim 1, wherein the phenylpropanolamine salt is made from phenylpropanolamine free base.

50. The process of claim 1, wherein the phenylpropanolamine salt is a salt of phenylpropylamine and an acid selected from the group consisting of: hydrofluoric acid, hydrochloric acid, hydrobromic acid, hydroiodic acid, sulfuric acid, phosphoric acid, nitric acid, formic acid, acetic acid, propionic acid, benzoic acid, tartaric acid, succinic acid, oxalic acid, malic acid, aspartic acid, and saccharic acid.

51. The process of claim 1, wherein the phenylpropanolamine salt is a salt of phenylpropylamine and an acid selected from the group consisting of carboxylic acid, dicarboxylic acid, and tricarboxylic acid.

52. The process of claim 1, wherein the phenylpropanolamine salt is a salt of phenylpropylamine and hydrochloric acid.

53. A process for making an O-acylated phenylpropanolamine salt of formula III useful in the manufacture of amphetamines

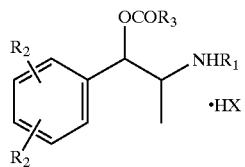

III from a phenylpropanolamine salt of formula II

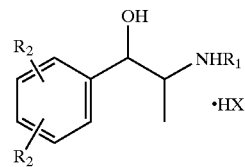

II wherein:
- $R_1$ is hydrogen or a lower alkyl group;
- each $R_2$ is independently a hydrogen, halogen, lower alkyl group, lower alkoxy groups, lower alkyl group substituted with 1 to 5 halogens, lower alkoxy groups substituted with 1 to 5 halogens, or both $R_2$ together constitute a —O(CH$_2$)$_x$O— where x is 1 to 4, thereby forming a ring structure fused with the phenyl group;
- $R_3$ is a $C_1$–$C_8$-alkyl group, a $C_1$–$C_{12}$-aralkyl group, $C_1$–$C_{12}$-alkaryl group, or a phenyl group, each optionally substituted by 1 to 5 substituents selected from halogen, hydroxy, or $C_1$–$C_6$-alkyl; and
- HX is an equivalent of an organic or inorganic acid, the process comprising acylating the phenylpropanolamine salt with an acylating agent to make a reaction mixture containing the O-acylated phenylpropanolamine salt.

54. A process for making compound of formula I

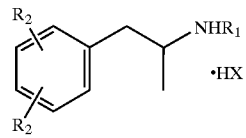

I from an O-acylated phenylpropanolamine salt of formula III

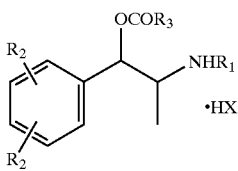

III wherein:
- $R_1$ is hydrogen or a lower alkyl group;
- each $R_2$ is independently a hydrogen, halogen, lower alkyl group, lower alkoxy groups, lower alkyl group substituted with 1 to 5 halogens, lower alkoxy groups substituted with 1 to 5 halogens, or both $R_2$ together constitute a —O(CH$_2$)$_x$O— where x is 1 to 4, thereby forming a ring structure fused with the phenyl group;
- $R_3$ is a $C_1$–$C_8$-alkyl group, a $C_1$–$C_{12}$-aralkyl group, $C_1C_{12}$-alkaryl group, or a phenyl group, each optionally substituted by 1 to 5 substituents selected from halogen, hydroxy, or $C_1$–$C_6$-alkyl; and
- HX is an equivalent of an organic or inorganic acid, the process comprising: hydrogenating the O-acylated phenylpropanolamine salt to make the compound of formula I.

* * * * *